(12) United States Patent
Lee et al.

(10) Patent No.: US 7,307,199 B2
(45) Date of Patent: Dec. 11, 2007

(54) PCR FAMILY GENES WHICH CONFER TOLERANCE TO HEAVY METALS

(75) Inventors: YoungSook Lee, Pohang (KR); Won Yong Song, Pohang (KR); InWhan Hwang, Pohang (KR); Do Young Kim, Pohang (KR); Eun Hwa Jeong, Pohang (KR); Eun Woon Noh, Suwon (KR); Young Im Choi, Suwon (KR); Enrico Martinoia, Zurich (CH); Joohyun Lee, Hanover, NH (US); Dongwoo Kim, Pohang (KR); Esther Vogt, Zurich (CH); Donghwan Shim, Pohang (KR); Kwan Sam Choi, Daejeon (KR)

(73) Assignees: POSCO, Pohang-shi (KR); POSTECH Foundation, Pohang (KR); POSTECH Academy-Industry Foundation, Pohang (KR)

( * ) Notice: Subject to any disclaimer, the term of this patent is extended or adjusted under 35 U.S.C. 154(b) by 0 days.

(21) Appl. No.: 10/907,694

(22) Filed: Apr. 12, 2005

(65) Prior Publication Data

US 2006/0230468 A1 Oct. 12, 2006

(51) Int. Cl.
C12N 15/09 (2006.01)
C12N 15/29 (2006.01)
C12N 15/82 (2006.01)
A01H 5/00 (2006.01)

(52) U.S. Cl. ............... 800/278; 800/298; 800/306; 800/317; 800/320.1; 435/468; 435/320.1

(58) Field of Classification Search ............ 800/278, 800/298, 295; 435/320.1, 468; 536/23.6
See application file for complete search history.

(56) References Cited

U.S. PATENT DOCUMENTS 5,364,451 A * 11/1994 Raskin et al. ............... 75/710

OTHER PUBLICATIONS

Ha et al . The Plant cell, vol. 11, pp. 1153-1163, (1999).*
Guerinot et al. Plant Physiology (2001), vol. 125, pp. 164-167.*
Peter Goldsbrough (1999), Ann Arbor Press, pp. 221-228.*
Salt et al. Biotechnology, vol. 13, pp. 468-474, 1995.*
Wong-Yong Song et al. Plant Physiology (2004), vol. 135, pp. 1027-1039.*
Mejáre and Bülow, "Metal-binding proteins and peptide in bioremediation and phytoremediation of heavy metals", TRENDS in Biotechnology, Feb. 2001; 19 (2):67-73.
Ensley, "Rationale for Use of Phytoremediation", Phytoremediation of Toxic Metals: Using Plants to Clean Up the Environment, 2000; 3-10.

* cited by examiner

*Primary Examiner*—Medina A Ibrahim
(74) *Attorney, Agent, or Firm*—JHK Law; Joseph Hyosuk Kim

(57) ABSTRACT

The present invention relates to novel Pcr family genes that confer tolerance to heavy metals to plants and microorganisms. More particularly, the present invention relates to novel Pcr family genes that confer tolerance to cadmium. The invention also relates to plant and microorganisms transformed with any of the Pcr genes thereby having improved resistance to and increased level of toxic materials, and methods of removing heavy metals from contaminated soil and water contaminated by growing the Pcr-transformed plants on the contaminated soils and water.

10 Claims, 7 Drawing Sheets

A

B

½ SG

C

½ SG + 30 µM Cd(II)

A

B

C

PCR FAMILY GENES WHICH CONFER TOLERANCE TO HEAVY METALS

BACKGROUND OF THE INVENTION (a) Field of the Invention

The present invention relates to a novel Pcr family gene which confers tolerance to heavy metal to organisms transformed with the Pcr family genes. More particularly, the present invention relates to a novel Pcr family gene which confers tolerance to heavy metal and transformed organisms using the gene thereby having improved resistance to and increased accumulation of toxic materials.

(b) Description of the Related Art

Heavy metals such as lead, cadmium, mercury and so on are major environmental toxicants, which cause reactive oxidation species generation, DNA damage, and enzyme inactivation by binding to active sites of enzymes in cells of living organisms.

Contamination of the environment with heavy metals has increased drastically due to industrialization and increase in population. Soils contaminated with heavy metals inhibit normal plant growth and cause contamination of foodstuffs. Many heavy metals are very toxic to human health and carcinogenic at low concentrations. Therefore removal of heavy metals from the environment is an urgent issue.

Studies for removing heavy metals from soil are actively progressing worldwide. Traditional methods of dealing with soil contaminants include physical and chemical approaches, such as the removal and burial of the contaminated soil, isolation of the contaminated area, fixation (chemical processing of the soil to immobilize the metals), and leaching using an acid or alkali solution. These methods, however, are costly and energy-intensive processes.

Living organisms have a mechanism for mitigating toxicity of materials using transporter proteins or biological materials having an affinity for noxious materials that invade the body. Use of genes contributing to living organism's resistance against noxious materials would provide an environmentally-friendly way to remediate environments polluted with noxious materials at a very low cost as compared with the physical and/or chemical remediation that is currently being employed (Mejare and Bulow, Trends in Biotechnology; 2001, Raskin I. and Ensley B. D. Phytoremediaton of Toxic Metals., John Wily & Sons, New York; 2000). In particular, as plants have many advantages such as their ability to express foreign genes readily and thus exhibit new phenotypes, they can be produced and maintained at a low cost, they are aesthetically pleasing, etc., research is being actively conducted on improvement of plants by inserting useful genes thereinto for use in environmental cleanup. This technique, the use of plants for cleaning up environment, is called "Phytoremediation." Phytoremediation has recently been proposed as a low-cost, environment-friendly way to remove heavy metals from contaminated soils. It is a relatively new technology for cleanup of contaminated soil that uses general plants, specially bred plants, or transgenic plants to accumulate, remove, or detoxify environmental contaminants. The phytoremediaton technology is divided into phytoextraction, rhizofiltration, and phytostabilization. Phytoextraction is a method using metal-accumulating plants to extract metals from soil into the harvestable parts of the plants; rhizofiltration is a method using plant roots to remove contaminants from polluted aqueous streams; and phytostabilization is the stabilization of contaminants such as heavy metals in soils to prevent their entry into ground water using plants.

Experiments were conducted to produce transgenic plants with improved capacity for phytoremediation. They used genes that confer resistance to heavy metals. Examples of heavy metal resistant genes are ABC (ATP Binding Protein) transporters such as YCF1, CAX2 (Calcium exchanger2), Cytochrome P450, NtCBP4 (*Nicotiana tabacum* calmodulin-binding protein), phytochelatin, glutathione synthetase, MerB (Organomercurial lyase) and so on. Since there are many different locations in the world that need phytoremediation, and since they are different in physical and biological conditions, there is a need to produce many different kinds of plants that can remediate the environment under different local conditions. Therefore, it is necessary to develop many transgenic plants transformed with diverse genes that work by different mechanisms that result in improved resistance to heavy metals and toxic compounds.

SUMMARY OF THE INVENTION

It is an aspect of the invention to provide Pcr family genes, which when expressed in plants confer improved tolerance to heavy metal and increased accumulation of heavy metals.

It is a further aspect of the invention to provide a recombinant vector harboring the Pcr family gene.

It is a further aspect of the invention to provide a transformant transformed with the Pcr family gene that has an improved tolerance to heavy metals and increased accumulation of heavy metals.

BRIEF DESCRIPTION OF THE DRAWINGS

in FIGS. 2B and 2C, "v" is control vector that does not contain Pcr family gene.

in FIG. 3B, S/X is a fragment where C-terminal of AtPcr1 protein was removed and S/K is a fragment which was separated using Sac 1 and Xho 1; fragment denoted as 5' is a portion obtained by cutting AtPcr1 with Ram Hl and fragment denoted as 3' is C-terminal portion remained by cutting AtPcr1 with Bam Hl.

in FIG. 5C a-e, GUS expression levels in leaf cells, not in root.

in FIG. 6A, C indicates liquid phase and M indicates cell membrane.

DETAILED DESCRIPTION OF THE PREFERRED EMBODIMENTS

Figure 1:
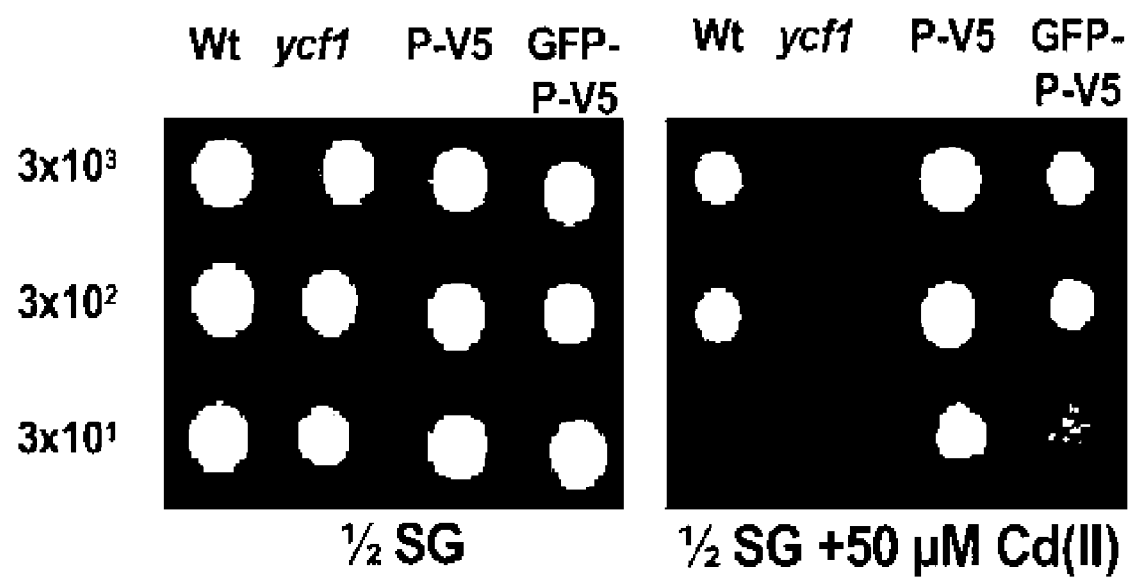
FIG. 1 shows the culture result in ½ SG-ura solid medium and ½ SG-ura solid medium including 50 uM of cadmium. Wt is wild type yeast, ycf1 is mutant yeast, P-V5 is transformed yeast where V5 tag gene is attached to Pcr1 gene, GFP-P-V5 is transformed yeast where green fluorescent protein is attached before the Pcr1 gene and V5 tag gene is attached after the Pcr1 gene.

The present invention relates to a gene that confers tolerance to and an ability to accumulate heavy metals, especially cadmium, a vector including the gene, and a transgenic cell and organism transformed with the gene.

The gene that confers tolerance to and increased accumulation of heavy metals is Pcr family gene which is found in *Arabidopsis*, tomato, petunia and rice plants. The Pcr family gene is exemplified by AtPcr1 (SEQ ID NO: 1), AtPcr2 (SEQ ID NO: 2), AtPcr8 (SEQ ID NO: 3), AtPcr9 (SEQ ID NO: 4), AtPcr10 (SEQ ID NO: 5), or OsPcr1 (SEQ ID NO: 6).

According to the preferred embodiment, the Pcr family gene is a gene expressing a protein which has a sequence homology of more than or equal to 29% with AtPcr1 protein. More preferably, the gene expresses a protein including a domain which has sequence homology of more than or equal to 35% with a transmembrane domain of AtPcr1.

When the Pcr gene is over-expressed in yeast, tolerance to heavy metal, especially cadmium, is significantly improved. In AtPcr1 protein expressed from AtPcr1 gene, a transmembrane domain plays a role in cadmium tolerance and the protein binds cadmium at biological membranes. In plants, the expression of the Pcr gene is increased by heavy metal and is tissue-specific. The expressed product is present in the plasma membrane.

If the Pcr gene is over-expressed in a plant, the content of cadmium in the shoot (e.g., leaves and trunks) is significantly increased. If the Pcr gene is over-expressed in a plant, heavy metal is transferred from root to shoot and is accumulated in the shoot. The accumulation of heavy metal in the shoot is very important in phytoremediation. If contamination material adsorbed by a plant is accumulated in roots, it is very difficult to harvest the contaminated root and remove the contaminated material, and it may be costly. However, if the contamination material is transferred to the shoot, it is convenient to remove the contaminated leaves and trunk. Therefore, the Pcr gene is useful since heavy metal, such as cadmium, is transferred from the root to shoot.

The present invention also provides a recombination vector including the gene, preferably a recombination vector including AtPcr1, AtPcr2, AtPcr8, AtPcr9, AtPcr10, or OsPcr1 genes. The examples of the recombination vector are pYES2/NTC-Pcr recombination vector or PGA1535-Pcr recombination vector. The preparation of the recombination vector is well known in this art.

The present invention also provides a transgenic organism transformed with the Pcr gene. The Pcr gene may confer cadmium tolerance and/or an increased ability to accumulate heavy metals (e.g. cadmium). Therefore, an organism transformed with the gene can cleanup soil and water contaminated by heavy metals economically and conveniently.

The transgenic organisms are preferably prokaryotic or eukaryotic organisms, for example, plants, animals, yeast, *E. coli* and fungus may be employed. Transgenic plants can be made to express heterologous DNA sequences using genetic engineering methods. The genes can be expressed in plant cells, plant tissues, or whole plant bodies. Plant transformants can be prepared according to known techniques, and *Agrobacterium tumefaciens*-mediated DNA transfer is typically employed. More preferably, recombinant *agrobacterium* constructed according to known genetic engineering techniques, can be introduced into plants using a method selected from the group consisting of biolistic bombardment, a dipping method, etc. In an embodiment of the present invention, transgenic plants can be prepared by constructing an expression cassette including a Pcr gene sequence which is operably linked to permit its transcription and translation, constructing a recombinant vector including the expression cassette, and introducing said recombinant vector into plant cells or plant tissues.

The above plants include herbaceous plants such as *Arabidopsis*, rice plant, rapes, leaf mustards, indian mustards, tobaccos, onions, carrots, cucumbers, sweet potatoes, potatoes, napa cabbages, radishes, lettuces, broccoli, petunias, sunflowers, grass, reed etc., and trees such as olive, willow, white birch, poplar, and birch. In some preferred embodiments, *Arabidopsis*, poplar, indian mustard, grass and rice plant are employed. In particular, tobaccos, sunflowers and poplar grow quickly, their root structures are large, and they are relatively easily transformed. Therefore, plants overexpressing Pcr genes can be used directly for environmental cleanup. For example, grass where Pcr gene is over-expressed may be used to cover a soil contaminated with heavy metals to make a safe and beautiful environment.

The transgenic plants can be asexually reproduced by tissue culture and grown into a plant according to conventional plant cell culturing methods and differentiation methods. The transgenic plants where the Pcr gene is over-expressed grow easily in a cadmium-containing medium, whereas plants where the gene expression is inhibited shows sensitivity to cadmium. The transgenic plants where Pcr gene over-expressed accumulate more cadmium in the shoot than a wild type of plant. In a plant used for cleanup of the environment, the accumulation of heavy metals in shoots make harvesting and treatment more convenient than accumulation in the roots.

The examples are presented herein to increase the understanding of the invention. The following examples, however, are provided solely in order for better understanding of the present invention: the present invention should not be construed to be limited thereto.

EXAMPLE 1

Cadmium Tolerance of Yeast Transformed with *Arabidopsis* AtPcr1 Gene

Wild type yeast, cadmium-sensitive mutant yeast (ycf1), and mutant yeast transformed with *Arabidopsis* AtPcr1 (P) gene (P-V5 and GFP-P-V5) were cultured in SD-ura solid media. Transformed yeast cells were again cultured in ½ SG-ura solid media including 30 to 100 uM of cadmium for 5 days. FIG. 1 shows the culture result in ½ SG-ura solid medium and ½ SG-ura solid medium including 50 uM of cadmium. In FIG. 1, Wt is wild type yeast, ycf1 is mutant yeast, P-V5 is transformed yeast where V5 tag gene is attached to Pcr1 gene, GFP-P-V5 is transformed yeast where green fluorescent protein is attached before the Pcr1 gene and V5 tag gene is attached after the Pcr1 gene. As shown in FIG. 1, the ycf1 mutant yeast did not grow in medium including 50 uM of cadmium as good as the wild type yeast whereas the yeast transformed with the Pcr1 gene of *Arabidopsis* grew as good as the wild type in medium including cadmium.

EXAMPLE 2

Other Pcr Family Genes Also Confer Cadmium Tolerance

Genes that have homology to AtPcr1 at the nucleotide base sequences and amino acid sequences were identified from database available. According to similarity of sequences, block diagram of FIG. 2A was prepared. AtPcr1, AtPcr2, AtPcr8, AtPcr9, AtPcr10 and OsPcr1 genes were separated using PCR method and ligated with pYES2/NTC vector to transform yeast. Using the transformed yeast, cadmium tolerance was experimented. Each primer used in PCR reaction is as follows: AtPcr1 (SEQ ID NO: 7; Pcr1-R1; 5'GAATTCATGGAAGCTCAACTTCATGCCAAG3', SEQ ID NO: 8; Pcr1-X1; 5'CTCGAGGCGGGTCATGC-CGCC3'), AtPcr2 (SEQ ID NO: 9; Pcr1-R1; 5'GAAT-TCATGGAAGCTCAACTTCATGCCAAG3', SEQ ID NO: 10; Pcr2; 5'TTTAACACTCGTAACAATGTGATCCA3'), AtPcr8 (SEQ ID NO: 11; 5'AACATATGAAT-TCATGGGTCGTGTCACTACTCCATC3', SEQ ID NO 12; 5'CTAAAATCAAACTCGAGCFFCGA-CATATATTGATTT3'), AtPcr9 (SEQ ID NO: 13; 5'ACCAAAAGAATTCATGTCCGAACAA-GAAGGCAAAAA3', SEQ ID NO: 14; 5'ATTTFGTGAT-GTCTCTGAGACGGTCCATGCCTGACGCTA3'), AtPcr10 (SEQ ID NO: 15; 5'CATCAGAGAATTCAT-GAAAGAGAAGAAGGGTCATTA3', SEQ ID NO: 16; 5'ATGAGACAAAGCTCGAGGTTAGCTGAT-TCCATGGTTT3'), OsPcr1 (SEQ ID NO: 17; OsPcr1-R1; 5'GAATTCATGTATCCCCCTGATCCGTCCAAGTCC3' OsPcr1-X1; SEQ ID NO: 18; 5'CTCGAGACCAAGGT-TAGGGTCGTGGCCGCGGTT3').

In order to measure cadmium tolerance, the transformed yeasts were cultured in ½ SG-ura solid media and ½ SG-ura solid media including 30 uM cadmium for 3 to 5 days. The results arc shown in FIG. 2B, In FIG. 2B , "v" is control where vector which does not contain Pcr family gene. In FIG. 2B, AtPcr1, AtPcr2, AtPcr8, AtPcr9, AtPcr10 and OsPcr1 genes are shown to confer cadmium tolerance. Of these cadmium tolerance genes, AtPcr10 has the lowest homology of about 29% with AtPcr1 (See sequence list). Therefore, genes that have 29% or higher homology with AtPcr1 are likely to confer cadmium tolerance when introduced into organisms.

EXAMPLE 3

Transmembrane Domain of AtPcr1 Protein Confers Cadmium Tolerance

Figure 3:
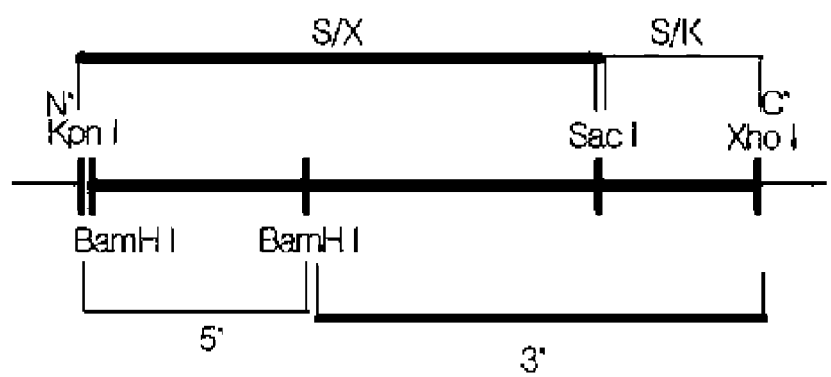
FIG. 3 is a restriction map of AtPcr1 protein fragments (A), and a photograph showing that AtPcr1 protein confers cadmium tolerance (B), and a photograph showing that the transmembrane domain of AtPcr1 protein confers cadmium tolerance (C)
Figure 3:
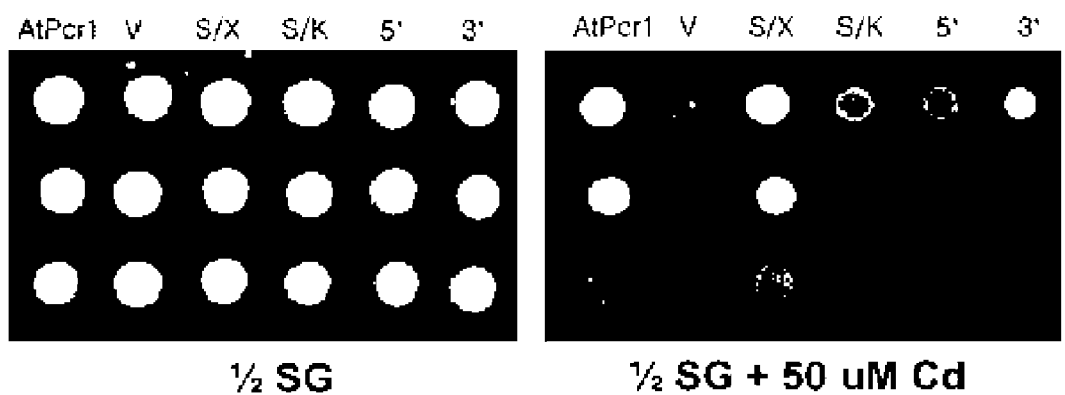
Figure 3:
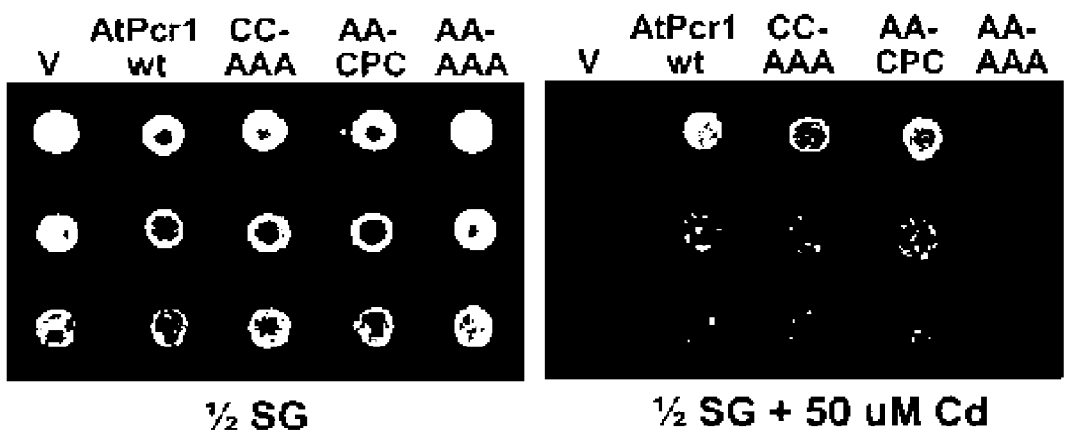

Fragments of AtPcr1 protein are shown FIG. 3A. In FIG. 3, S/X is a fragment where C-terminal of AtPcr1 protein was removed and S/K is a fragment which was separated using Sac I and Xho I. Fragment denoted as 5' is a portion obtained by cutting AtPcr1 with Bam HI and fragment denoted as 3' is C-terminal portion remained by cutting AtPcr1 with Bam HI.

After yeasts were transformed with the fragments of AtPcr1 protein, cadmium tolerance was evaluated by culturing them in cadmium-containing medium. The results are shown in FIG. 3B. After yeasts were transformed with the fragments of AtPcr1 protein where CC-CC of transmembrane domain was substituted by other amino acids, cadmium tolerance was evaluated by culturing them in cadmium-containing medium. The results are shown in FIG. 3C. As shown in FIG. 3B, S/X which corresponds to the transmembrane domain plays an important role in cadmium tolerance. As shown in FIG. 3C, CC-CPC amino acids which are positioned in the transmembrane domain are also important in cadmium tolerance. When the sequences of cadmium tolerant Pcr gene family members are compared at the transmembrane domain, AtPcr10 has the lowest homology of about 35% with AtPcr1 (See sequence list). Therefore, genes that have 35% or higher homology in the transmembrane domain with AtPcr1 are likely to confer cadmium tolerance when introduced into organisms.

EXAMPLE 4

AtPcr1 Protein Binds With Cadmium

Figure 4:
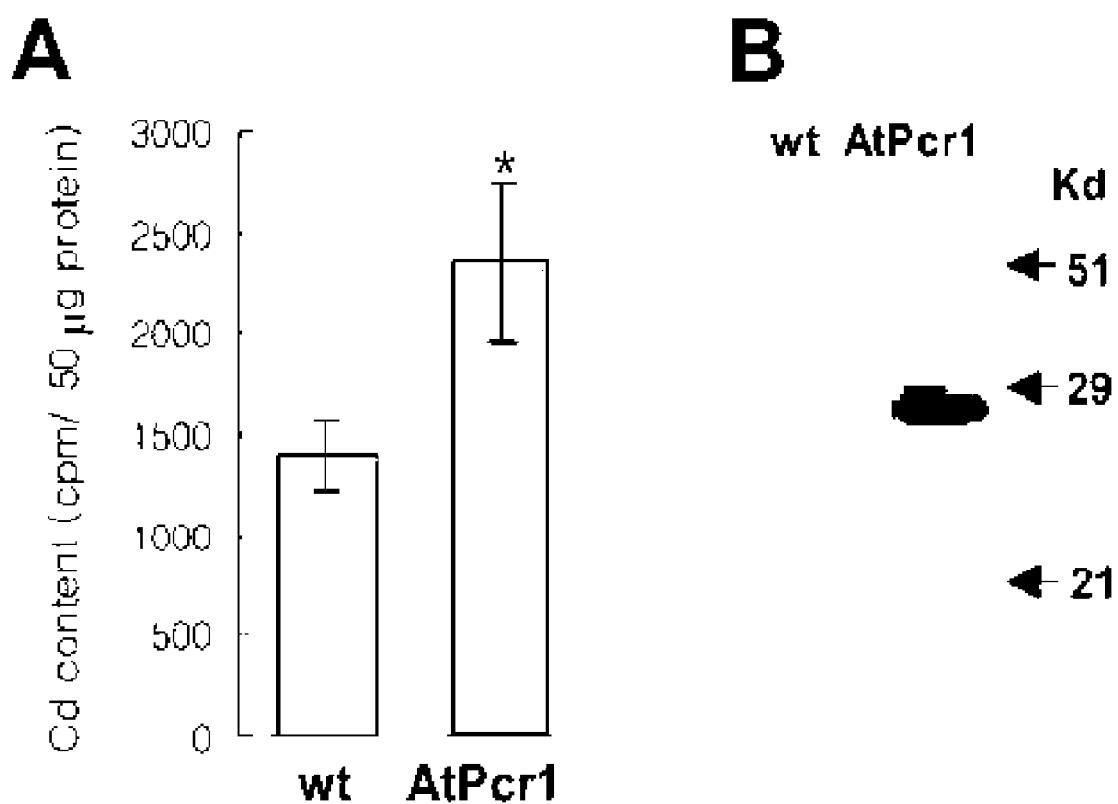
FIG. 4 is a graph showing that AtPcr protein stimulates the binding of biological membrane with cadmium (A) and a Western blot photograph showing that the AtPcr protein in an experiment is present in biological membrane (B)

Biological membranes were separated from wild type yeast and yeast where AtPcr1 was over-expressed and cultured in a solution including 10 uM of cadmium (including isotope) for 15 minutes. The cultured medium was passed through nitrocellulose membrane having 0.45 um of pore size and washed with 10 mM Tris-HCl (pH 8.0) solution four times. Then the radioactivity of the biological membranes was measured using gamma ray measuring equipment. The results are shown in FIG. 4A. In FIG. 4A, AtPcr1 expression increased the amount of cadmium binding to the biological membrane of yeast.

Proteins of the separated biological membrane were separated using SDS-PAGE electrophoresis and an amount of the produced protein was measured using western blotting. The results are shown in FIG. 4B. In FIG. 4B, it is assured that Pcr1 proteins are expressed in the biological membrane of yeast.

EXAMPLE 5

Expression of AtPcr1 and AtPcr2 Genes in *Arabidopsis* Plant (1) Total RNA separation; *Arabidopsis* plants cultured for 3 to 8 weeks were treated with cadmium for 0 hour, 5 hours and 20 hours, separated into shoots and roots, and ground using liquid nitrogen. Then total RNA extraction buffer (0.25 M Tris HCl pH 9.0, 0.25 M NaCl, 0.05 M EDTA, 0.345 M p-aminosalicylic acid, 0.027 M truisopropyl naphthalene sulfonic acid, 0.02% beta-mercaptoethanol, 0.024% phenol) and phenol/chloroform in the same amount of the buffer were added and mixed. After they were centrifuged at 12,000 rpm for 10 minutes, the obtained supernatant was transferred to a new tube and isopropanol was added in an amount of six times the volume relative to the supernatant. Centrifugation was again performed at 12,000 rpm for 10 minutes, RNA was precipitated, and dissolved in water treated with DEPC (diethyl pyrocarbonate) and then kept in a freezer.

Figure 5:
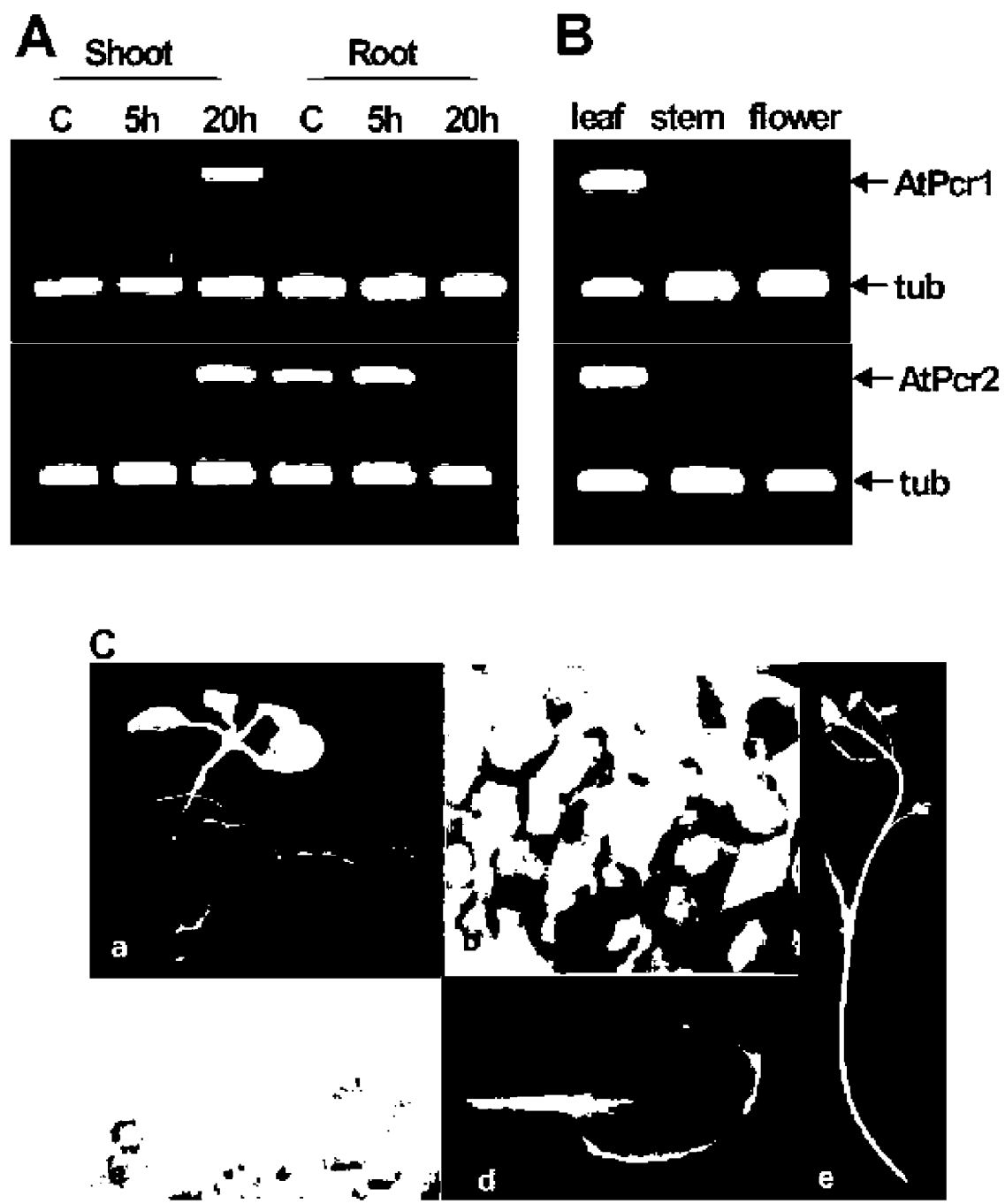
FIG. 5 is a photograph showing that expression of AtPcr1 and AtPcr2 genes is increased by cadmium (A) and photographs showing the expression is tissue-specific expression (B, C)

(2) RT-PCR reaction; Using a Superscript First-strand Synthesis System for RT-PCR kit (Invitrogen), cDNA was synthesized from total RNA. Using AtPcr1 primer (SEQ ID NO: 7; 5'GAATTCATGGAAGCTCACTTCATGCCAAG3', 5'TTTAACACTCGTAACAATTGTGATCCA3'), AtPcr2 primer (SEQ ID NO: 9; 5'GAATTCATGGAAGCTCAACTTCATGCCAAG3', and SEQ ID NO: 10; 5'TTTAATTCTTGTAACCAAATAGTGGAATAT3'), the PCR reaction was performed to evaluate gene expression. The results are shown in FIGS. 5A and B. In FIGS. 5A and B, tub is the expression control where tubulin gene was expressed. As shown in FIGS. 5A and B, when wild type *Arabidopsis* was treated with cadmium, expression of AtPcr1 and AtPcr2 genes increased in shoots and expression of the AtPcr2 gene increased in roots.

(3) Preparation of AtPcr1 promoter:GUS transformed plant; In order to prepare the AtPcr1 promoter:GUS construct, upstream sequence, 3.2 kb of coding sequence was obtained by PCR (PCR primer; SEQ ID NO: 19; 5'CTGTTTGTTTTTGAAAGCTAGCACATGAGT3', SEQ ID NO: 20; 5'TGAAGGTGTTGAGGATCCAAGAAGAGAG3') using genomic DNA of *Arabidopsis*. After the PCR product was cut with the restriction enzyme Nhe I and Bam HI, it was Transferred to pB1101 binary vector, and then injected into *Arabidopsis* plant by dipping method. T2 generation plant selected by Kanamycin was used in GUS analysis. The GUS analysis results are shown in FIG. 5C. In FIG. 5C, a ten-day *Arabidopsis* was treated with 100 uM of cadmium for 2 days (a to c), and an 8 week cultured *Arabidopsis* was not treated with cadmium (d). In FIG. 5C-*a*, GUS is shown in leaves and is not shown in root. As a result of measuring mesophyll cells (shown in FIG. 5C-*b*) and guard cells (shown in FIG. 5C-*c*) in the leaves, there are a large number of GUSs but there are a small number of GUSs in cuticle cells surrounding the mesophyll cells and guard cells. As shown in FIG. 5C-*d*, a large number of GUSs are shown in cauline and resette leaves and in FIG. 5C-*e*, low expression of GUS is shown in the trunk and the pedicel of a blooming plant.

EXAMPLE 6

Figure 6:
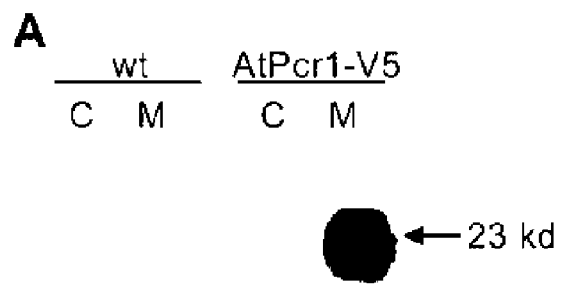
FIG. 6 is a Western blot photograph (A) and a fluorescent protein photograph (B) showing AtPcr1 protein is present in a plasma membrane of a cell of *Arabidopsis*.
Figure 6:

Measurement of Expression Position of AtPcr1 Protein in Cell (1) Western blot; In order to separate protein from AtPcr1 transformed yeast and *Arabidopsis*, extraction buffer (50 mM Hepes-KOH pH 7.4, 5 mM MgCl$_2$, 1 mM EDTA, 10 mM DTT, 0.7 ug/mL pepstain A, 5 ug/mL aprotinin, 20 ug/mL leupeptin, 0.5 mM Phenylmethylsulfonyl fluoride) was injected and mixed well. Centrifugation was performed at 12,000 rpm for 5 minutes. After supernatant was obtained, centrifugation was performed at 100,000 g for 1 hour again, so that membrane and liquid of cell were separated. 10 to 50 ug of proteins were separated with SDS-PAGE and transferred to nitrocellulose membrane. The membrane was dipped in a 1×TBST (0.1% Tween 20 in 1×TBS) solution including 7.5% nonfat milk for 1 hour. Washing with 1×TBST solution was performed for 5 minutes twice, and then reaction with anti-V5 antibody was performed for 3 hours at room temperature. Then, washing with 1×TBST solution was performed for 15 minutes three times and reaction with sheep anti-mouse IgG conjugated horseradish peroxidase was performed for 1 hour and washing with 1×TBST solution was performed three times. Using ECL (Amersham Pharmacia Biotech) solution, protein expression signal was detected with x-ray film. The results are shown in FIG. 6A. In FIG. 6A, C indicates liquid phase and M indicates cell membrane. From FIG. 6A, AtPcr1 protein is confirmed to be localized in cell membrane of plant.

(2) Protein expression in plant protoplast; Green fluorescent protein (GFP protein) gene was linked after AtPcr1 gene to obtain GFP-AtPcr1. GFP-AtPcr1 was ligated with pGA1535 vector to transform the plant *Arabidopsis* plant transformed by culturing for 2 to 3 weeks was cut and incubated in 30 ml enzyme solution (1% cellulase R-10, 0.25% mercerozyme R-10, 0.5 M mannitol, 10mM MES, 1 mM CaCl, 5 mM beta-mercaptoethanol, 0.1% BSA, pH 5.7 to 5.8). And then, vacuum infiltration was performed for 10 minutes with 150 mmHg and cultured for 5 hours in 22° C. dark room agitating at 50to 75 rpm. Protoplasts were filtered using 100 um of mesh (SIGMA S0770), concentration gradient (21% sucrose) centrifugation was performed 730 rpm for 10 minutes with respect to the protoplasts resulting in complete separation of protoplase. The separated protoplast was suspended in 20 ml of W5 solution (154 mM NaCl, 125 mM CaCl2, 5 mM KCl, 5 mM glucose, 1.5 mM MES, pH 5.6) and centrifugation was performed at 530 rpm for 6 minutes to precipitate protoplasts. The precipitated protoplasts were resuspended with W5 solution and placed on ice for 30 minutes. In order to measure a location of protein in protoplasts, fluorescence was measured using a fluorescence microscope (Axioskop2 Fluorescence microscope, Zeiss). In FIG. 6B, on the right is one using optical microscope and on the left is one using fluorescence microscope. From FIG. 6B, AtPcr1 protein is located in the protoplast plasma membrane of a plant. From the above, AtPcr1 protein is located in protoplast plasma membrane of the plant.

EXAMPLE 7

Preparation of Transformed *Arabidopsis* Where AtPcr Gene is Over-Expressed (1) Culture of plants for transformation; *Arabidopsis* for transformation was treated at low temperature of 4° C. for two days and then was grown for 3-4 weeks until flower stalks rose, varying temperature of 22° C./18° C. with photoperiod of 16/8 hours (day/night).

(2) Preparation of the construct for over-expressing AtPcr1 gene and AtPcr1 activation line selection; in order to over-express AtPcr1 gene, gene in pYES2/NTC vector was cut with restriction enzyme Hind III and Pme I and ligated with plant binary vector, pGA1535(Sense-AtPcr1). AtPcr1 activation line was selected from the *Arabidopsis* mutant pool having activation-tag, which was distributed from the University of Wisconsin, Biotechnology Center.

(3) Preparation of the construct for inhibiting AtPcr1 gene expression; In order to inhibit AtPcr1 and AtPcr2 gene expression, AtPcr1-antisense vector was prepared. AtPcr1 was cut out from pYES2/NTC-AtPcr1-V5 vector using Bam HI and Xba I enzymes and the AtPcr1 fragment was inserted into pGA1535 vector which was cut using Bgl II and Xba I enzymes (Antisense-AtPcr1).

(4) Transformation; Vectors having AtPcr1 gene (Sense-AtPcr1, AtPcr1-antisense) were introduced into agrobacterium using electroporation. The agro-bacterium was cultured in 1 liter of YEP medium (Yeast extract 10 g, NaCl 5 g, Peptone 10 g, pH 7.5) until O.D 600 value approached 0.8 to 1.0. Culture solution was centrifuged to harvest cells and was suspended in 1 liter of MS medium including 5% sucrose, and Silwet L-77 (LEHLE SEEDS, USA) was added at a concentration of 0.01% immediately before transformation. Only shoot parts of Arabidopsis was dipped in a solution including agrobacterium for 1 to 2 minutes to induce transformation.

Figure 7:
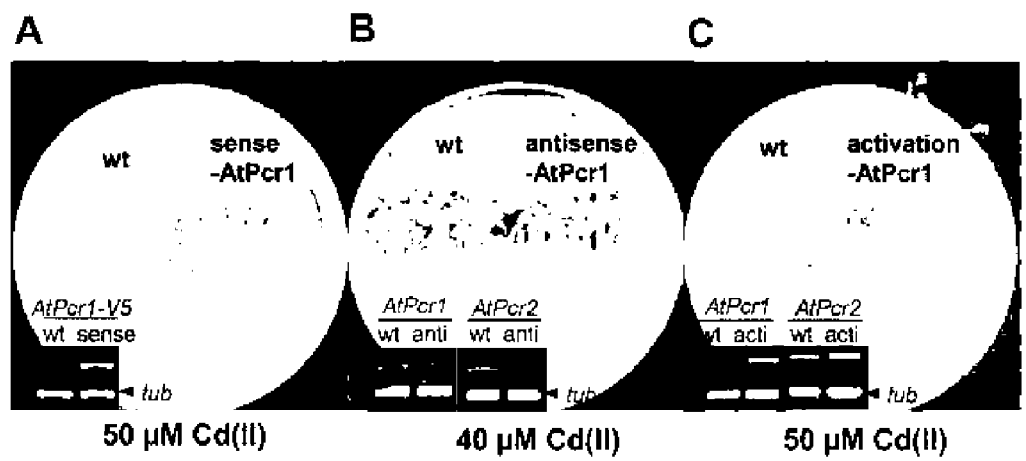
FIG. 7 is a series of photographs showing that a cadmium tolerance is improved when transformed *Arabidopsis* where AtPcr1 gene is over-expressed is grown in cadmium-containing medium (A, C) when compared to the wild type and a photograph showing that plant where AtPcr1 gene expression is inhibited is more sensitive to cadmium (B)

(5) Evaluation of cadmium tolerance of transformed plants: Arabidopsis transformed with sense-AtPcr1 and AtPcr1 Activation line were grown in media including 50 uM of cadmium, and Arabidopsis transformed with Antisense-AtPcr1 vector was grown in medium including 40 uM of cadmium. The results are shown in FIGS. 7A-C. As shown in FIGS. 7A and C, Arabidopsis transformed with sense-AtPcr1 and AtPcr1 Activation line grew better than wild type (wt). On the contrary, as shown in FIG. 7B, Arabidopsis transformed with Antisense-AtPcr1 vector grew slower than wild type (wt). The expression levels of AtPcr1 and AtPcr2 genes in these transformed plants are inserted in FIGS. 7A to C. Inserted figure in FIG. 7A indicates that the amount of AtPcr1 mRNA in sense-AtPcr1 plant is higher than that in wild type (wt). Inserted figure in FIG. 7B indicates that the amounts of AtPcr1 and AtPcr2 mRNAs in antisense-AtPcr1 plant are lower than those in wild type (wt). Inserted figure in FIG. 7C indicates that the amounts of AtPcr1 and AtPcr2 mRNAs in activation-AtPcr1 plant are higher than those in wild type (wt). As a result of investigating the relation between the above gene expression level and growth rate in cadmium-containing medium, Arabidopsis (sense-AtPcr1, activation-AtPcr1) where AtPcr gene is expressed at high level relative to wild type has improved cadmium tolerance compared to wild type, whereas Arabidopsis (antisense-AtPcr1) where AtPcr gene is expressed at low level relative to wild type is more sensitive to cadmium than wild type.

EXAMPLE 8

Measurement of Accumulation Amount of Heavy Metal in Transformed Plant

Figure 8:
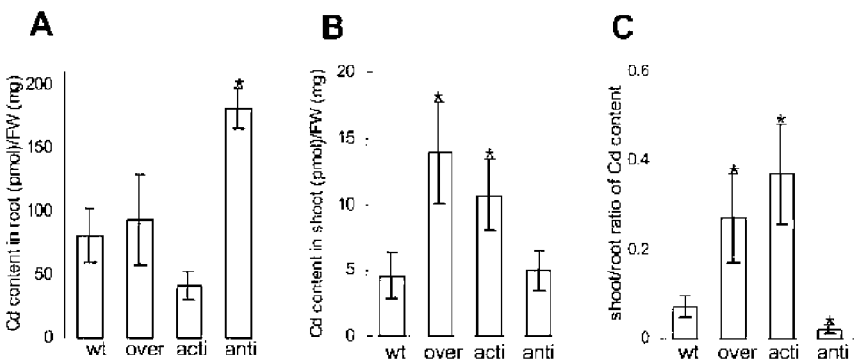
FIG. 8 is graphs showing cadmium contents accumulated in root (A) and shoot (B) of *Arabidopsis*, and the content ratio of shoot/root (C), indicating that *Arabidopsis* where AtPcr1 and AtPcr2 genes are over-expressed accumulates more cadmium in its shoot than wild type.

In order to measure the amount of accumulation of heavy metals in plants, plants transformed with AtPcr1 gene of Example 7 were cultured in ½ MS solid media for 10 days and then transferred to ⅕ MS liquid media including 20 uM of cadmium and a small amount of radioisotope and cultured for 1 hour. Cultured plants were harvested and washed with 1 mM of cool citric acid solution for 20 minutes and separated into shoot and root regions. The cadmium amount of the separated plants was measured using gamma ray measuring equipment. The results are shown in FIG. 8. In FIG. 8, "over" indicates Sense-AtPcr1 Arabidopsis plant of Example 7, "anti" indicates activation-tagged line of Example 7, "anti" indicates antisense-AtPcr1 Arabidopsis of Example 7. From the results of FIG. 8, it is confirmed that Arabidopsis where AtPcr gene is over-expressed accumulates more cadmium in shoot regions than wild type (wt).

EXAMPLE 9

Preparation of Transformed Poplar and Tobacco Where AtPcr Gene is Over-expressed (1) Transformation: PGA1535-AtPcr1 vector having AtPcr1 gene was introduced into agrobacterium and then was used for transforming poplar and tabacco.

Transformation of poplar: Agrobacterium was cultured in a medium including antimicrobial agents and centrifuged. Stem tissues of poplar was cut into 5 to 7 mm sized pieces from seedlings grown for one month, so as not to include axillary buds using a sharp scalpel. Then 5 ml of saline solution (0.85% NaCl) was added into a petri-dish and the cut stem tissues were incubated. Supernatant of the centrifuged agrobacterium was discarded to obtain a precipitate and the precipitate was resuspended in 25 ml of saline solution. 30 ul of acetosyringone (10 mg/ ml) per 30 ml of saline solution was added and the prepared tissues were dipped in agrobacterium suspension for 15 minutes. To remove bacteria from the tissue surface, the tissue was put into a tube containing saline solution and after gentle shaking, was picked with a pair of forceps to transfer to a new tube. Finally, the tissue was pulled out and placed on distilled paper to remove moisture. The tissue was cultured in callus induction medium (MS+2,4-D 1 mg/l+BA 0.01 mg /l) which does not include antimicrobial agent for 2 days, and transferred to callus induction medium including antimicrobial agent and cultured for 2 weeks. The callus was transferred to a fresh medium plate every 2 weeks. Callus was induced within 4 weeks after culture. When its size is about 2 to 3 mm, it was transferred to a shoot induction medium including an antimicrobial agent. The shoot thus developed was transferred to a root induction medium including an antimicrobial agent and propagated.

Transformation of tobacco: Leaves of tobacco which were grown for one month was cut into thumb finger-nail sized pieces, and placed with backside of the leaves upward on a callus induction medium. Two hundred ul of previously grown agrobacterium was spread evenly on the tissue, and they were cultured at 28° C. for three days, sealed with wrap and foil. The tissue was washed with water until bacteria were mostly removed and transferred to a medium including antimicrobial agents. It was cultured in dark for 3 days, and transferred to a shoot induction medium, and cultured for one month. The induced shoot was transferred to a root induction medium to induce roots. Seedlings with shoots and roots were transferred to soil and grown further.

Figure 2:
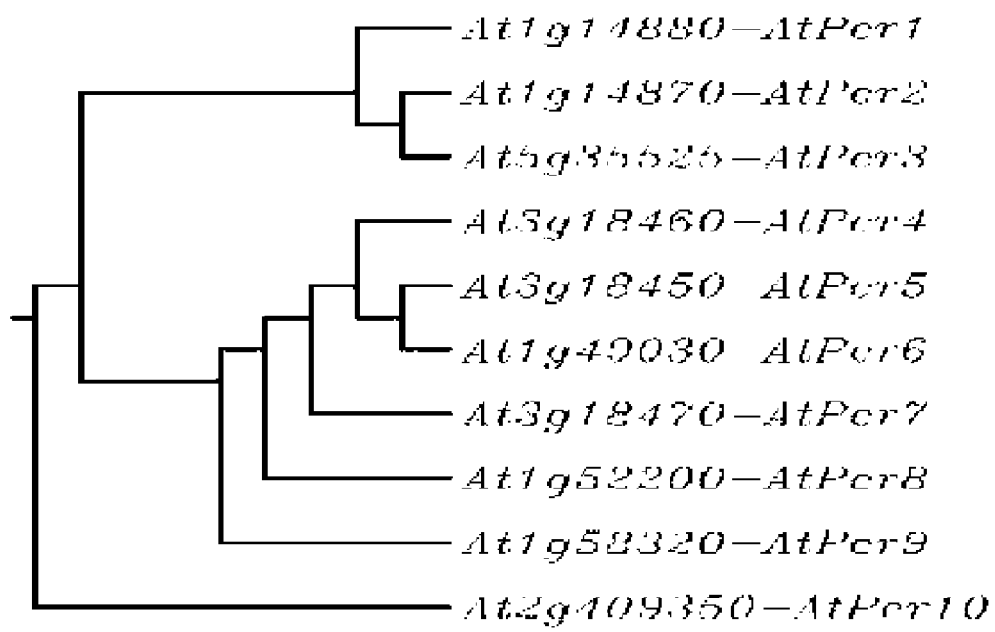
FIG. 2 is a block diagram of AtPcr family genes (A) and photographs showing that yeast over-expressing the gene has cadmium tolerance (B, C)
Figure 2:
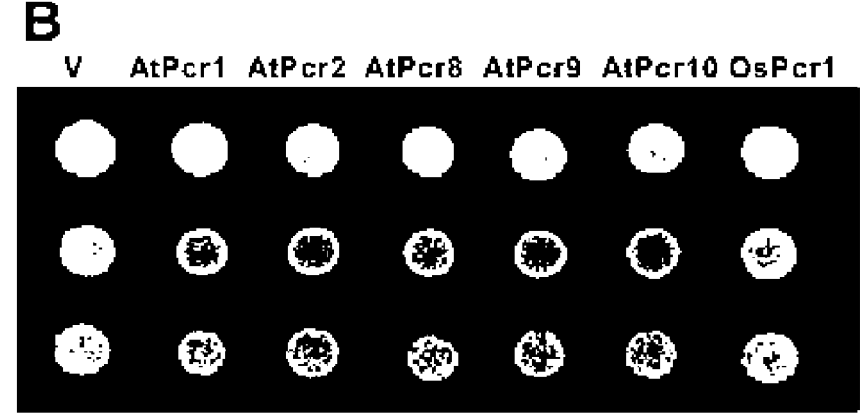
Figure 2:
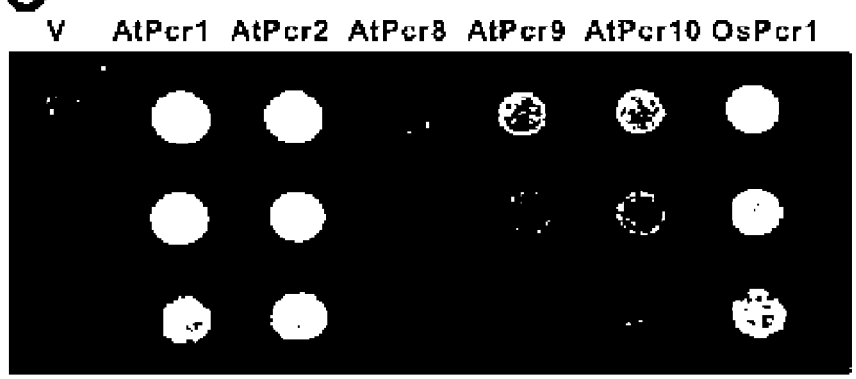
Figure 9:
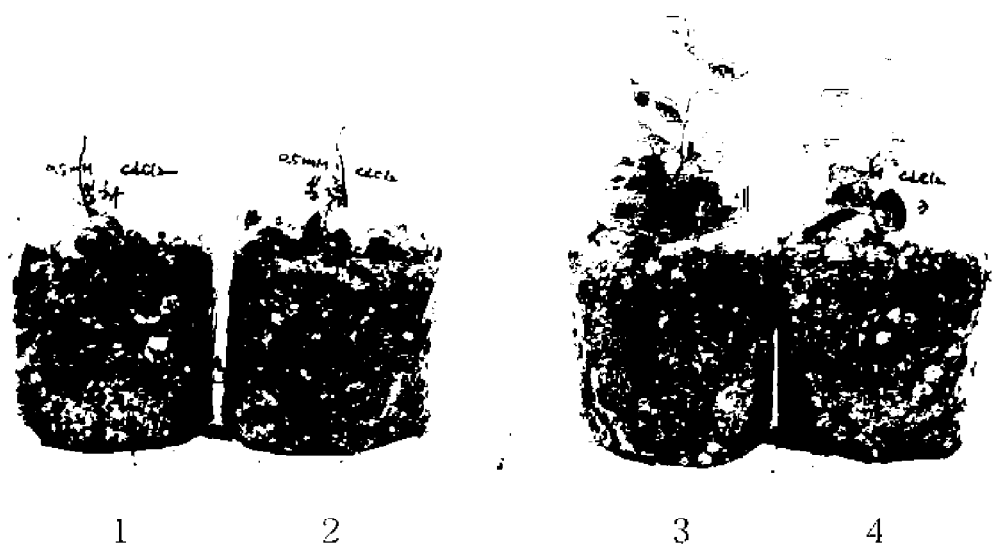
FIG. 9 is a photograph showing that poplar where AtPcr1 gene is over-expressed has significantly more improved growth than wild type in cadmium-containing soil, wherein 1 and 2 are the results of a culture of a wild type poplar in soil containing 0.5 mM of cadmium and 3 and 4 are the results of culture of AtPcr1-transformed poplar in soil including 0.5 mM of cadmium for 3 weeks.

(2) Evaluation of cadmium tolerance of the transformed poplar: A soil including vermiculite and perlite mixed in a ratio of 1:1 was dipped in cadmium-containing solution for 10 minutes. The transformed poplar seedlings were placed in the soil and their cadmium tolerance was evaluated. The results are shown in FIG. 9. In FIG. 9, 1 and 2 are the results of a culture of a wild type poplar in soil containing 0.5 mM of cadmium and 3 and 4 are the results of culture of AtPcr1-transformed poplar in soil including 0.5 mM of cadmium for 3 weeks. From the results of FIG. 9, it is clear that cadmium tolerance of AtPcr1-transformed poplar is improved relative to wild type poplar.

As described above, Pcr genes of the present invention confers tolerance to heavy metals, especially cadmium and an ability to accumulate heavy metals. A transformed plant which has improved tolerance to and an ability to accumulate heavy metals in a shoot region can be obtained by introducing the gene to many different plants. If the Pcr gene is introduced to a plant with a large biomass and growth rate, soil and water contaminated with heavy metals can be remedied in an environment-friendly and economical manner.

What is claimed is:

1. An isolated Pcr (plant cadmium resistance) nucleic acid sequence selected from the group consisting of SEQ ID NO: 1, SEQ ID NO: 2, SEQ ID NO: 3, SEQ ID NO: 4, and SEQ ID NO: 5.

2. A recombinant vector comprising the Pcr nucleic acid sequence according to claim 1.

3. A transformed prokaryotic organism, plant or yeast with improved heavy metal tolerance and/or increased accumulation of heavy metals, as compared to a wild type prokaryotic organism, plant or yeast of the same species, which is transformed with the vector according to claim 2.

4. The transformed prokaryotic organism, plant or yeast according to claim 3, wherein the plant is a herbaceous plant or tree plant.

5. The transformed prokaryotic organism, plant or yeast according to claim 3, wherein the plant is selected from the group consisting of Arabidopsis thaliana, rice, rapes, leaf mustard, Indian mustard, tobacco, onion, carrot, cucumber, sweet potatoes, potatoes, napa cabbage, radish, lettuce, broccoli, petunia, sunflower, grass, reed, olive, willow, white birch, poplar, and birch.

6. The transformed prokarvotic organism, plant or yeast according to claim 3, wherein the plant is a transformed plant which accumulates more heavy metals in a shoot region than wild type plant.

7. An isolated Pcr (plant cadmium resistance) nucleic acid sequence comprising SEQ ID NO: 6.

8. A recombinant vector comprising the Pcr nucleic acid sequence according to claim 7.

9. A transformed prokaryotic organism, plant or yeast with improved heavy metal tolerance and/or increased accumulation of heavy metals, as compared to a wild type prokaryotic organism, plant or yeast of the same species, which is transformed with the vector according to claim 8.

10. The transformed prokarvotic organism, plant or yeast according to claim 3, wherein the prokarvotic organism is a bacterium.

* * * * *

SEQUENCE LISTING

<160> NUMBER OF SEQ ID NOS: 20

<210> SEQ ID NO 1
<211> LENGTH: 750
<212> TYPE: DNA
<213> ORGANISM: Arabidopsis thaliana

<400> SEQUENCE: 1

```
attgctttct atttaaaaac ctctttattt ttctctccat ggaagctcaa cttcatgcca      60
agcctcatgc tcaaggagaa tggtccacag gcttctgtga ttgcttctct gactgccgaa     120
actgttgtat cacattatgt tgtccatgta tcacatttgg ccaagtcgct gagattgtag     180
atcgaggatc caaatcgtgt tgtgcggctg gagcattata catgttgata gacttaataa     240
caagttgtgg gcgtatgtac gcgtgtttct atagtggaaa gatgagagct caatacaata     300
ttaaaggaga tggttgtact gattgcctta aacattttg ctgtaacctc tgtgctttga      360
cccaacaata ccgtgaactc aagcaccgcg gtttcgatat gagccttgga tgggcaggga     420
acgcagagaa acaacaaaat caaggtggag tggcgatggg tgctccagcc ttccaaggcg     480
gcatgacccg ctaagattga tttctctatg tgatcatcat ttgtcttatg tgtaataaaa     540
acgaggttta atcctctgtc gtgtgtgtat gtgttgtgta atcttctgtt tgttttttgaa    600
agtttgaaca tgagtatttc tttaatgtat atcccaatgt aatggatcac aattgttacg     660
agtgttaaat tacaacgtcg ataaagttac accaaaacaa tacttacgtc ctttttatgg     720
atgttaggtt atttggtcgt tctattcgtc                                      750
```

<210> SEQ ID NO 2
<211> LENGTH: 708
<212> TYPE: DNA
<213> ORGANISM: Arabidopsis thaliana

<400> SEQUENCE: 2

```
tacaaaacct tacattgctt tccatttaaa actctcttct tctttttgt tctctctctc       60
tcttcatgga agctcaacac cttcatgcca agcctcatgc tgaaggagaa tggtccacag     120
gcttctgtga ttgcttttct gactgcaaaa attgttgtat cacattctgg tgtccatgta     180
tcacctttgg ccaagtcgcc gagattgtag atcgaggatc cacatcgtgt ggtactgctg     240
gagctctata cgcgttgata gccgtagtaa ctggttgtgc atgtatatac tcatgttct      300
atcgtggaaa gatgagagct caatataata ttaaaggaga tgattgtact gattgcctta     360
aacatttctg ctgtgagctt tgttctttga cccaacaata ccgtgaactc aagcaccgcg     420
gttacgatat gagtcttgga tgggcgggga acgtggagag acaacagaat caaggaggtg     480
tggccatggg tgctccggtc ttccaaggcg gcatgacccg ctaagaatta tttctttatg     540
taattcattt gtcttttata tgtagtaata aaacgaggtt taatcctctg tttgtgttgt     600
taatatgctt gttgtgattt gaacaaaaaa aaatgcttgt tgtgaaagtt tagacataca     660
gtatatgaat gttcttcat tgtatattcc actatttggt tacaagaa                   708
```

<210> SEQ ID NO 3
<211> LENGTH: 764
<212> TYPE: DNA
<213> ORGANISM: Arabidopsis thaliana

<400> SEQUENCE: 3

```
aaccaaaaat tcttcgtct ctgtctccaa aatcgaatca aaatctctaa agtttcaatt        60
```

-continued

| | |
|---|---|
| tttttgttct gttctttta ttttttaaa gaatggcttc aatttctgca actttgcctt | 120 |
| cgccattgtt actcacacag agaaaatcca atctcacatc gattcaaaaa ctcccatttt | 180 |
| ctctaactcg aggtacgaat gatcttctc cattatctct tactcgaaac cctagcagca | 240 |
| tcagtctgat ggtgaaagct agtggagaaa gctcagattc atcgactgat ctcgacgttg | 300 |
| ttagtacgat tcagaatgtt tgggataagt ctgaagatag gttaggtctt attggtttgg | 360 |
| gttttgctgg tattgtagct ctttgggcat cattgaatct catcacggca atcgacaaat | 420 |
| tgcccgttat ctcgagcgga ttcgaactag ttggtatctt gttctccacg tggttcacat | 480 |
| atcgatatct cttgttcaaa ccggacagac aggagctttc gaaaattgtc aagaaatcag | 540 |
| tagcggatat acttggccag tgaaccttgt gtgtgtgata atacttcatc tttggaagat | 600 |
| gatttgtttg caagtttgta aaattacatg acagggtggt tgttgtttct agtccaataa | 660 |
| tgtcatgcat ttgaaacctg taaatacttt attgttggtt tttggttgtg agcaaaatca | 720 |
| atcttttcta atttcaaaga ttctctttta tgattatacg tttt | 764 |

<210> SEQ ID NO 4
<211> LENGTH: 447
<212> TYPE: DNA
<213> ORGANISM: Arabidopsis thaliana

<400> SEQUENCE: 4

| | |
|---|---|
| atgtccgaac aagaaggcaa aaatgagaag aaagtaactg aagggcaatg gactaccggt | 60 |
| ttatacgact gtctctctga agatatctct acatgctgct ttacatgggt ttgtccttgc | 120 |
| gttgcatttg ggaggatcgc tgagatcctt gataaaggag aaacaagtcg aggacttgct | 180 |
| ggattaatgg tggtcgcaat gtctagcatt gggtgtggag ggtactatgc ttcaaaatac | 240 |
| agagccaaat tgaggcatca atacgctttg cccgaggcgc cttgtgccga tggcgccatt | 300 |
| cactgcttct gctgtccatg tgctcttact caagaacacc gcgaactcaa acatcgaggt | 360 |
| cttgatccct ctctagggtg gaacattgag aatggaggat taaacagcaa cacgcccccg | 420 |
| tttgtagcgt caggcatgga ccgttaa | 447 |

<210> SEQ ID NO 5
<211> LENGTH: 793
<212> TYPE: DNA
<213> ORGANISM: Arabidopsis thaliana

<400> SEQUENCE: 5

| | |
|---|---|
| gttctctctt ccgatccttt ttttgtctct gcttcttgct ctgctctgtg gtaaataaag | 60 |
| tcctgttctt gatattggtg gtttcatcag aattaggatg aaagagaaga agggtcatta | 120 |
| cgtgccacca tcttatattc cattaacaca gtcagatgct gatactgaag tagagaccac | 180 |
| tactccaaat ctggaaattg ctgtttctga agcacaaaaa gatgatccga dacaatggtc | 240 |
| atctggtata tgcgcttgct tcgacgatat gcagagctgt tgtgtaggtt tgttctgtcc | 300 |
| ttgttatatc tttggcaaaa acgcagagct tctggggtct ggaacatttg caggaccctg | 360 |
| cttaacccat tgcatctcct gggctttggt caataccatt tgctgctttg caactaatgg | 420 |
| cgcattgctc ggtctaccgg gatgcttgt gtcatgttat gcttgcgggt accgcaaatc | 480 |
| attaagagcc aagtacaatt tacaggaggc tccatgtggg gattttgtaa cacacttctt | 540 |
| ctgtcacttg tgtgccattt gccaagaata cagagagatt cgagaacaaa gcagtggttc | 600 |
| atatcctctt gacatgaaga tggctatcac caatgccccc ttggctcaaa ccatggaatc | 660 |

```
agctaactga tcactttgtc tcattgagct tccttgttta ttttgtagaa gacattttc      720 ttttcatcga cttttgcaat gtatttgaga agtttgatga gtaagtaaaa ctttctaagg     780
taatttatca tat                                                         793
```

```
<210> SEQ ID NO 6
<211> LENGTH: 756
<212> TYPE: DNA
<213> ORGANISM: Oryza sativa (japonica cultivar-group)

<400> SEQUENCE: 6
agctaattaa ggtaccagca actccatcac atccttaatt tgcagcagca ggtaattgta      60
caccggcgaa ggaaattaaa ggaaagtagg agatcgatgg ccaagccaag cgccgccgcc     120
tggtccaccg gcctcttgga ctgcttcgac gactgcggcc tatgtacgtc ctcgtcctcg     180
ccgccggccg ccgtgccatg gctagatcat atgcaaatcc tccgtagtac tactaatgca     240
gtagccgtag ctgacacgtg ggttcggatc cccacgttaa tgtctactac tacatcagca     300
gtagtgcaga taatctctac tgtgctagat catatcatga acactgattc gttagttctg     360
atctgtaact aacttattag ttcacattga tctgcaggct gcatgacgtg ctggtgcccg     420
tgcatcacgt tcgggcgggt ggcggagatg gtggacaggg ggtcgacgtc gtgcggcacc     480
agcggcgcgc tgtacgcgct gctggcgacg gtcaccggct gccagttcgt ctactcctgc     540
gtctaccggg gcaagatgcg cgcccagtac ggcctcggcg acgacgccgc ctgcgccgac     600
tgctgcgtcc acttctggtg caacaagtgc gcgctgtgcc aggagtaccg cgagctcgtc     660
gcccgcggct acgaccccaa gctcggatgg gacctcaacg tccagcgcgg cgccgccgcc     720
gccgcagcgc cgccgtgca gcacatgggc cgttaa                                756
```

```
<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
gaattcatgg aagctcaact tcatgccaag                                       30
```

```
<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ctcgaggcgg gtcatgccgc c                                                21
```

```
<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
gaattcatgg aagctcaact tcatgccaag                                       30
```

```
<210> SEQ ID NO 10
<211> LENGTH: 26
```

```
<212> TYPE: DNA
<213> ORGANISM: Artificial Sequence
<220> FEATURE:
<223> OTHER INFORMATION: primer

<400> SEQUENCE: 10
tttaacactc gtaacaatgt gatcca                                        26

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
aacatatgaa ttcatgggtc gtgtcactac tccatc                             36

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
ctaaaatcaa actcgagctt cgacatatat tgattt                             36

<210> SEQ ID NO 13
<211> LENGTH: 36
<212> TYPE: DNA
<213> ORGANISM: Artificial Sequence
<220> FEATURE:
<223> OTHER INFORMATION: primer

<400> SEQUENCE: 13
accaaaagaa ttcatgtccg aacaagaagg caaaaa                             36

<210> SEQ ID NO 14
<211> LENGTH: 38
<212> TYPE: DNA
<213> ORGANISM: Artificial Sequence
<220> FEATURE:
<223> OTHER INFORMATION: primer

<400> SEQUENCE: 14
atttgtgatg tctctgagac ggtccatgcc tgacgcta                           38

<210> SEQ ID NO 15
<211> LENGTH: 36
<212> TYPE: DNA
<213> ORGANISM: Artificial Sequence
<220> FEATURE:
<223> OTHER INFORMATION: primer

<400> SEQUENCE: 15
catcagagaa ttcatgaaag agaagaaggg tcatta                             36

<210> SEQ ID NO 16
<211> LENGTH: 37
<212> TYPE: DNA
<213> ORGANISM: Artificial Sequence
<220> FEATURE:
<223> OTHER INFORMATION: primer

<400> SEQUENCE: 16
```

-continued atgagacaaa gctcgaggtt agctgattcc atggttt                                37

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17
gaattcatgt atccccctga tccgtccaag tcc                                    33

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
ctcgagacca aggttagggt cgtggccgcg gtt                                    33

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
ctgtttgttt ttgaaagcta gcacatgagt                                        30

<210> SEQ ID NO 20
<211> LENGTH: 28
<212> TYPE: DNA
<213> ORGANISM: Artificial Sequence
<220> FEATURE:
<223> OTHER INFORMATION: primer

<400> SEQUENCE: 20
tgaaggtgtt gaggatccaa gaagagag                                          28